(12) United States Patent
Liu

(10) Patent No.: US 11,559,704 B2
(45) Date of Patent: Jan. 24, 2023

(54) MR IMAGE-GUIDED RADIATION CONTROLLING DEVICE

(71) Applicant: Medical Intelligence Medizintechnik GmbH, Schwabmünchen (DE)

(72) Inventor: Rui Liu, Augsburg (DE)

(73) Assignee: MEDICAL INTELLIGENCE MEDIZINTECHNIK GMBH

( * ) Notice: Subject to any disclaimer, the term of this patent is extended or adjusted under 35 U.S.C. 154(b) by 758 days.

(21) Appl. No.: 16/356,756

(22) Filed: Mar. 18, 2019

(65) Prior Publication Data
US 2019/0290933 A1   Sep. 26, 2019

(30) Foreign Application Priority Data
Mar. 22, 2018   (EP) .................................... 18163246

(51) Int. Cl.
*A61N 5/10*      (2006.01)
*A61B 5/00*      (2006.01)
*A61B 5/055*     (2006.01)
*G01R 33/48*     (2006.01)
*G01R 33/30*     (2006.01)
*G01R 33/565*    (2006.01)

(52) U.S. Cl.
CPC .......... *A61N 5/1049* (2013.01); *A61B 5/0036* (2018.08); *A61B 5/0042* (2013.01); *A61B 5/0055* (2013.01); *A61B 5/055* (2013.01); *A61B 5/682* (2013.01); *A61B 5/6814* (2013.01); *A61N 5/10* (2013.01); *A61N 5/1067* (2013.01); *G01R 33/307* (2013.01); *G01R 33/4808* (2013.01); *G01R 33/565* (2013.01); *A61B 2562/182* (2013.01); *A61B 2562/225* (2013.01); *A61N 2005/1055* (2013.01); *A61N 2005/1057* (2013.01); *A61N 2005/1074* (2013.01)

(58) Field of Classification Search
CPC .... A61B 5/055; A61B 5/6814; A61N 5/1049; A61N 2005/1055
See application file for complete search history.

(56) References Cited

U.S. PATENT DOCUMENTS

| 4,746,864 A | * | 5/1988 | Satoh | G01R 33/56563 324/309 |
| 5,549,616 A | * | 8/1996 | Schulte | A61B 90/16 5/622 |

(Continued)

FOREIGN PATENT DOCUMENTS

EP         3289973 A1        3/2018

OTHER PUBLICATIONS

European Patent Office; Communication pursuant to Article 94(3) EPC for application 18163246.4, dated Mar. 27, 2020.

(Continued)

*Primary Examiner* — Jason M Ip
(74) *Attorney, Agent, or Firm* — Quarles & Brady LLP

(57) ABSTRACT

There is provided a patient's cranial position monitoring and controlling device for controlling a magnetic resonance (MR) guided radiation source module via an MR-guided radiation controlling device connected to the patient's cranial position monitoring and controlling device and an MR-guided radiation system including a patient's cranial position monitoring and controlling device, which allows for better MR-imaging while allowing patient position monitoring close to the patient.

9 Claims, 5 Drawing Sheets

(56) References Cited

U.S. PATENT DOCUMENTS

| | | | |
|---|---|---|---|
| 6,542,767 B1 * | 4/2003 | McNichols | A61B 18/20 600/407 |
| 7,907,987 B2 * | 3/2011 | Dempsey | G01R 33/4808 378/65 |
| 2007/0167724 A1 * | 7/2007 | Gadagkar | A61B 5/055 600/410 |
| 2008/0136418 A1 * | 6/2008 | Renz | G01R 33/3657 324/322 |
| 2010/0072997 A1 * | 3/2010 | Fischer | G01R 33/3621 324/309 |
| 2015/0265216 A1 | 9/2015 | Andrews et al. | |

OTHER PUBLICATIONS

Extended European Search Report issued in priority European Application No. EP18163246, dated Oct. 4, 2018. 5 pages.

* cited by examiner

MR IMAGE-GUIDED RADIATION CONTROLLING DEVICE

CROSS-REFERENCES TO RELATED APPLICATIONS

This application claims the benefit of EP Application No. 18 163 246.4 filed Mar. 22, 2018. The contents of that application are hereby incorporated by reference for all purposes as if set forth in their entirety herein.

FIELD OF THE INVENTION

The present invention relates to a magnetic resonance image-guided radiation controlling device, a magnetic resonance image-guided radiation controlling system and corresponding components having a reduced field-related impact on magnetic resonance imaging.

BACKGROUND OF THE INVENTION

Medical imaging is commonly used to assist in the diagnosis and/or treatment of patients. Magnetic resonance imaging (MRI) is an example of a medical imaging technology that is often performed during the diagnosis and treatment of tumors. This leads to the situation, that the magnetic resonance imaging is performed at the same time of diagnosis and treatment of patients, so that there is a need to establish compatibility of the components used for treatment of the patient and the magnetic resonance imaging process. In other words, when performing a magnetic resonance imaging (MRI), it is desired to reduce any relevant impact on the MR-imaging device. This can be achieved according to already known systems in that the treatment room having positioned therein the MR-imaging device and the patient is a shielded room, and other components, e.g. for monitoring the patient's position and a linear accelerator (LINAC) gating are positioned outside this shielded room so that any external impact on the MR-Imaging can be reduced to a minimum in order to avoid artefacts during imaging.

However, when using MR-imaging during treatment of a patient, in particular when applying a radiation treatment of tumors, it is desired to have a proper positioning of the patient during treatment to avoid unintended injuries of the patient resulting from radiation treatment. Accordingly, it is not only desired to provide a proper positioning of the patient, but also to monitor the patient's position and to become aware of when the positioning is no longer appropriate or sufficiently exact for a radiation treatment. For this purpose, it is desired to have systems, which monitor the patient positioning. However, there is the risk that such devices for patient position monitoring produce an undesired electromagnetic noise which may influence the MR-imaging. Therefore, such monitoring and positioning devices are located outside of the above mentioned shielded room where the MR-imaging takes place in order to avoid any influence thereon.

There may be a need to provide a patient's cranial position monitoring and controlling device which can be positioned closer to the MR-imaging device and to the patient to simplify the monitoring and surveillance of the patient, however, without having the impact from such a patient cranial position monitoring and controlling device onto the MR-imaging.

SUMMARY OF THE INVENTION

The present invention provides a patient's cranial position monitoring and controlling device as well as a magnetic resonance-guided radiation system, which reduces the impact on a magnetic resonance imaging whilst providing a sufficient monitoring of the patient.

According to an embodiment of the invention, there is provided a patient's cranial position monitoring and controlling device for controlling a magnetic resonance-guided radiation source module via an MR-guided radiation controlling device to be connected to the patient's cranial position monitoring and controlling device, wherein the patient's cranial position monitoring and controlling device comprises an MR-guided radiation controlling module, a patient's cranial position monitoring module, and an interface module, wherein the patient's cranial position monitoring module is communicatively connected to the MR-guided radiation controlling module, wherein the interface module has an inward side and an outward side, wherein the inward side is communicatively connected to the MR-guided radiation controlling module and the outward side is connectable to the MR-guided radiation controlling device, wherein the patient's cranial position monitoring module is adapted for receiving a signal indication for a patient's cranial position during MR-guided radiation treatment by the MR-guided radiation source module; wherein the interface module is adapted for separating an inward communication of the patient's cranial position monitoring and controlling device from an outward communication of the patient's cranial position monitoring and controlling device with respect to MR-imaging relevant electromagnetic noise produced within the patient's cranial position monitoring and controlling device, wherein the MR-guided radiation controlling module is adapted for controlling the MR-guided radiation source module via the MR-guided radiation controlling device to be connected to the outward side of the interface module based on an output of the patient's cranial position monitoring module.

Thus, a structure can be provided, which reduces or avoids emission from a patient's cranial position monitoring and controlling device, in particular emission coming from a communication of the patient's cranial position monitoring and controlling device with other devices, like for example an MR-guided radiation controlling device, which may control an MR-guided radiation source module. This allows positioning of a patient's cranial position monitoring and controlling device close to a patient, in particular within a shielded room where the MR-imaging takes place. As the interface module separates an inwardly directed communication and an outwardly directed communication of the patient's cranial position monitoring and controlling device with respect to MR-imaging relevant noise, which may result from electric and electronic devices within the patient's cranial position monitoring and controlling device. Accordingly, the patient's cranial position monitoring and controlling device can be located directly beside a patient, in order to monitor the position of the patient, and does not need to be provided in a separate room which is shielded over the MR-imaging room. Thus, it is possible to reduce electronic noise and to avoid artefacts associated with imaging, so-called MRI artefacts.

According to an embodiment of the invention, the interface module comprises an optical-signal-to-electrical-signal-converter having an electrical inward side and an optical outward side, wherein the optical-signal-to-electrical-signal-converter is adapted to convert an electrical signal into an optical signal and vice versa; wherein the electrical inward side is connected to the MR-guided radiation controlling module and the optical outward side is connectable to the MR-guided radiation controlling device.

Thus, it is possible to keep any electric signal within the patient's cranial position monitoring and controlling device and to use an optical communication line to communicate or receive any signal to or from an MR-guided radiation controlling device, which may be located in a separate room apart from the patient's cranial position monitoring and controlling device. In particular, signal transmissions regarding the controlling of an MR-guided radiation source module can be carried out via the optical communication line. It should be understood, that the controlling of the MR-guided radiation controlling device or the MR-guided radiation source module via the MR-guided radiation controlling device may also include a shutdown signal to shut down the MR-guided radiation source module to prevent radiating, if, for example, the patient's cranial position monitoring and controlling device detects that the patient has left its intended position. An optical signal does not generate an electric or magnetic field, which may have any impact on the MR-imaging.

According to an embodiment of the invention, the interface module comprises a wire-wireless/wireless-wire converter having a wire bounded inward side and a wireless bounded outward side, wherein the wire-wireless/wireless-wire converter is adapted to convert a wire bound signal to a wireless signal and vice versa, wherein the wire bound inward side is connected to the MR-guided radiation controlling module and the wireless outward side is connectable to the MR-guided radiation controlling device.

Thus, it is possible to establish a communication line between the patient's cranial position monitoring and controlling device and the MR-guided radiation controlling device which has no or at least a reduced impact on the MR-imaging. The wireless transmission may be configured according to the IEEE 802.11 specifications, with a minimum frequency of 2.4 GHz so as to avoid generation of imaging artefacts with, for example a 1.5 T MR scanner or MR-imaging device. It should be understood, that a patient's cranial position monitoring and controlling device may be provided with either an optical/electrical converter as described above or a wire/wireless converter or with both, an optical/electrical converter and a wire/wireless converter at the same time.

According to an embodiment of the invention, the interface module comprises a filter module having an inward side and an outward side, wherein the filter module comprises a filter arrangement being adapted to filter MR-imaging relevant noise produced within the patient's cranial position monitoring and controlling device between the inward side and the outward side, wherein the inward side is connected to the MR-guided radiation controlling module and the outward side is connectable to the MR-guided radiation controlling device.

Thus, the interface having a filter module may filter all critical components from a signal being communicated from the patient's cranial position monitoring and controlling device to an MR-guided radiation controlling device. The remaining, i.e. filtered signal may be created in a form, that no or at least a very reduced impact on the MR-imaging can be expected.

According to an embodiment of the invention, the patient's cranial position monitoring and controlling device comprises a shielding cover, adapted to attenuate an MR-imaging relevant noise produced within the patient's cranial position monitoring and controlling device for avoiding MR-imaging artefacts at an MR-imaging module.

Thus, also electromagnetic noise generated within the patient's cranial position monitoring and controlling device can be absorbed or at least attenuated so as to reduce any significant impact from the patient's cranial position monitoring and controlling device onto an MR-imaging. The attenuation of the shielding cover may be in the range of about 100 dB with respect to the MRI relevant frequency range of an electrical or magnetic field generated by the internal components of the patient's cranial position monitoring and controlling device. This allows to position the patient's cranial position monitoring and controlling device closer to the patient which simplifies monitoring of the position without entering the risk of disturbing the MR-imaging. The attenuation of at least 100 dB is related to the MRI resonant frequency with respect to the electromagnetic noise emitted by the electrical components within the patient's cranial position monitoring and controlling device.

According to an embodiment of the invention, the patient's cranial position monitoring module of the patient's cranial position monitoring and controlling device comprises a patient's cranial position sensor and a terminal for a patient's cranial position sensing device to be connected and to be applied to the patient, wherein the patient's cranial position sensor is adapted to monitor a patient's cranial position during MR-guided radiation treatment with the MR-guided radiation source module, wherein the MR-guided radiation controlling module is adapted for controlling the MR-guided radiation source module via the MR-guided radiation controlling device to be connected to the interface module based on a patient's position sensed by the patient position sensor. According to an embodiment of the invention, the MR-guided radiation controlling module is adapted for instructing the MR-guided radiation controlling device to shut down an MR-guided radiation source of an MR-guided radiation source module.

Thus, the patient's cranial position monitoring and controlling device can be provided with a sensing facility and a coupling unit in form of a terminal to couple an external patient cranial position sensing device. It should be noted that the patient's cranial position sensing device does not need to include any electrical components, which may have an impact on the MR-imaging, but have a more or less mechanical set up in order to allow sensing of a patient's position by the patient's cranial position sensor within the patient's cranial position monitoring and controlling device.

According to an embodiment of the invention, the patient's cranial position monitoring and controlling device comprises a positive or negative pressure operated patient's cranial position sensing device and a pressure generating module for providing the patient's cranial position sensing device with a positive or negative pressure, wherein the patient's cranial position sensing device is connectable to the pressure generating module via the terminal for the patient's cranial position sensing device, wherein the patient's cranial position sensor is a pressure sensor for detecting via the terminal a pressure or pressure change at the patient's cranial position sensing device with which pressure or pressure change being dependent on the patient's cranial position.

Thus, the patient's cranial position monitoring and controlling device can be directly provided with a patient's cranial position sensing device, which may be releasable, detachable or fixedly connected to the terminal so as to allow monitoring of a patient's position. The patient's cranial position sensing device may be a pressure or vacuum, i.e. positive or negative pressure operated duct arrangement, which allows it to sense a patient's position based on a pressure or vacuum change, which pressure or vacuum change may be recognized by the patient's cranial position sensor. To provide the patient's cranial position sensing device with a required positive or negative pressure, the pressure generating module may generate a positive or negative pressure within the cranial position sensing device, so that the patient's cranial position sensor may detect any change in the pressure or vacuum. If the patient's cranial position sensing device does not include any electrical or magnetic components which may generate a noise which may impact the MR-imaging, any electrical devices can be maintained within, for example, the shielding and within any interface boundary of the patient's cranial position monitoring and controlling device.

According to an embodiment of the invention, the patient's cranial position sensing device comprises a pressure volume, a duct connecting the pressure volume to the terminal and a ventilation opening being formed in the pressure volume of the patient's cranial position sensing device, wherein the pressure sensor is adapted to detect a pressure change in the pressure volume of the patient's cranial position sensing device depending on the coverage of the ventilation opening.

Thus, a patient's cranial position sensing device may be provided which has no magnetic or electrical components, as it is fully positive or negative pressure operated. The pressure-generating module may generate the positive pressure or a vacuum in the pressure volume of the patient's cranial position sensing device, which is communicatively connected via a duct to the pressure sensor so that any change in pressure upon release of the ventilation opening may change the entire pressure in the patient's cranial position sensing device, which change in pressure may be sensed by the pressure sensor. It should be noted, that this design of a patient's cranial position sensing device allows that all electric or magnetic components which may be relevant with respect to generating an MR-imaging relevant noise may be kept within the boundaries of the patient's cranial position monitoring and controlling device, in particular within the shielding thereof.

According to an embodiment of the invention, the patient's cranial position sensing device is formed as a mouthpiece having a pressure volume formed therein and being connected to the terminal via the duct, wherein the mouthpiece has a ventilation opening formed therein, so that when the mouthpiece is in a predetermined patient's position, the ventilation opening is covered by a patient's anatomy, in particular the palate, so that a pressure change occurs in the pressure volume upon release of the patient's anatomy, in particular the palate, from the ventilation opening.

As the mouthpiece, in particular an individualized patient-related mouthpiece provides a reliable reference with respect to the patient's cranial anatomy, a mouthpiece is a reliable reference for position monitoring. As the mouthpiece is connected to the patient's palate, wherein the palate may cover the ventilation opening, any release of the palate from the mouthpiece will release a cover of the ventilation opening and therefore result in a pressure change in the entire system which may be monitored by the pressure sensor.

According to an embodiment of the invention, the patient's cranial position monitoring module comprises an emergency sensor and a terminal for an emergency button to be connected, wherein the MR-guided radiation controlling module is adapted for controlling the MR-guided radiation controlling device to be connected via the interface module, based on an emergency button's signaling, in particular for instructing the MR-guided radiation controlling device to shut down an MR-guided radiation source of an MR-guided radiation device or MR-guided radiation source module.

Thus, an emergency system may be provided close to the patient, so that either an assistant like a medical care person or the patient itself may activate an emergency button, which may be connected via the terminal to the emergency sensor to, for example, shut down the MR-guided radiation. This may be required for example if the patient should feel uncomfortable or has unexpected pain during treatment. It should be noted, that also the emergency button to be connected to the terminal for the emergency button may be operated free of any electric or magnetic components. In particular, the emergency button may be a pressure-operated device, like for example a balloon which can be pressed by a patient, so that the emergency sensor may detect this change of pressure in the emergency system as an indication for an emergency case. In this case, the emergency sensor can also be a pressure sensor.

According to an exemplary embodiment, there is provided an MR-guided radiation system comprising a patient's cranial position monitoring and controlling device as described in the embodiments above, an MR-guided radiation controlling device for controlling an MR-guided radiation source module to be connected and a signal communication line having a first end and a second end, wherein the MR-guided radiation controlling device comprises an MR-guided radiation controlling module and an interface module, wherein the interface module has an inward side and an outward side, wherein the inward side is communicatively connected to the MR-guided radiation controlling module, wherein the interface module is adapted for coupling an inward communication of the MR-guided radiation controlling device to an outward communication of the MR-guided radiation controlling device, wherein the MR-guided radiation controlling module is adapted for controlling an MR-guided radiation source module to be connected based on an input received from the patient's cranial position monitoring and controlling device via the outward side of the interface module, wherein the signal communication line is connected with its first end to the outward side of the patient's cranial position monitoring and controlling device and with its second end to the outward side of the MR-guided radiation controlling device.

Thus, an entire MR-guided radiation system may be provided which includes both, a patient's cranial position monitoring and controlling device, which may be positioned close to a patient during MR-guided radiation treatment, as well as an MR-guided radiation controlling device, which may be an MR-LINAC gating, which may directly control a radiation source and other components to be connected to the MR-guided radiation controlling device. The MR-guided radiation controlling device may be located separately and separated by a shielding from the patient's treatment room, particularly the MR-imaging so as to avoid any impact from the MR-guided radiation controlling device onto the MR-imaging. As the communication between the patient's cranial position monitoring and controlling device on the one hand and the MR-guided radiation controlling device on the other hand is conducted via a communication line which may be an optical communication line or a wireless communication or a line having a filtered signal transmission, an impact from the signals being transmitted via the communication line, even within the treatment room will have not have a noise impact on the MR-imaging.

According to an embodiment of the invention, also the interface module of the MR-guided radiation controlling device may comprise an optical-signal-to-electrical-signalconverter having an electrical inward side and an optical outward side, wherein the optical-signal-to-electrical-signal-converter is adapted to convert an electrical signal into an optical signal and vice versa, wherein the electrical inward side is connected to the MR-guided radiation controlling module and the optical outward side is connectable to the patient's cranial position monitoring and controlling device. The purpose of the interface module on the MR-guided radiation controlling device site is analogue to the function of the interface module on the patient's cranial position monitoring and controlling device site. The same applies for the interface module which may be in the form of a wire-wireless/wireless-wire converter as described above with respect to the patient's cranial position monitoring and controlling device. The same applies for an interface module having a filter module as described above with respect to the patient's cranial position monitoring and controlling device. It should be noted that also the MR-guided radiation controlling device may have a shielding cover which may be adapted to attenuate an MR-imaging relevant noise produced within the MR-guided radiation controlling device for avoiding artefacts at an MR-imaging device. However, in case the MR-guided radiation controlling device is located apart and probably separately shielded in a room, the direct shielding of the MR-guided radiation controlling device may have a lower attenuation factor as long as the impact on the MR-imaging will be kept at a minimum.

According to an embodiment of the invention, the MR-guided radiation controlling module of the MR-guided radiation controlling device is adapted for controlling, in particular shutting down an MR-guided radiation imaging module to be connected based on an input received from a patient's cranial position monitoring and controlling device via the output site of the interface module of the MR-guided radiation controlling device.

Thus, it is possible not only to control or shut down the MR-guided radiation, but also the MR-guided radiation imaging module, so that no imaging takes place if it is not required. This may avoid a later separation of imaging data which have been generated during the time, where the MR-guided radiation source had already been shut down.

According to an embodiment of the invention, the signal communication line comprises one of a non-conductive, in particular an optical connection and a wireless transmission connection between the first end and the second end.

Thus, the signal communication line can be avoided from generating a noise which may impact the MR-imaging. It should be noted that the signal communication line does not mandatorily have to be a physical communication line. In particular in case of a wireless signal communication, the communication line may be an air interface having no physical carrier like a glass fiber or a wire.

According to an embodiment of the invention, the MR-guided radiation system comprises a first room and a second room, wherein the patient's cranial position monitoring and controlling device is located in the first room and the MR-guided radiation controlling device is located in the second room, wherein the first room is separate to and shielded by a shielding over the second room with respect to an MR-imaging relevant noise emitted by the MR-guided radiation controlling device, wherein the signal communication line transits from the first room to the second room through the shielding.

Thus, an impact of the MR-guided radiation controlling device onto an MR-imaging can be reduced not only by a shielding of the MR-guided radiation controlling device and/or a shielding of the patient's cranial position monitoring and controlling device as such, but also by a shielding between two separate rooms.

According to an embodiment of the invention, the MR-guided radiation system further comprises a power supply being located in the second room and a filtering device being located between the first room and the second room, wherein the patient's cranial position monitoring and controlling device is connected to the power supply via the filtering device, wherein the filtering device is adapted to filter MR-imaging relevant noise of the power supply voltage.

Thus, even if the patient's cranial position monitoring and controlling device is power supplied by a grid, the impact of the supply voltage may be reduced using a filtering device. It should be noted, that the patient's cranial position monitoring and controlling device may also be operated by a battery power supply which then may avoid a grid power supply and consequently a filtering device. However, a patient's cranial position monitoring and controlling device may also be provided with both, a grid power supply and a battery power supply, which may respectively serve as a redundant set up to maintain a patient's monitoring, even if a grid power supply should break down.

It should be noted, that embodiments as described above may be combined with respect to each other so as to gain a synergetic effect, which may extend over the separate technical effects of the single features. Exemplary embodiments of the present invention will be described in the following.

BRIEF DESCRIPTION OF THE FIGURES

Exemplary embodiments of the invention will be described in the following with reference to the following figures.

DETAILED DESCRIPTION OF EXEMPLARY EMBODIMENTS

In the following, a detailed description of exemplary embodiments will be given to explain the invention in more detail.

Figure 1:
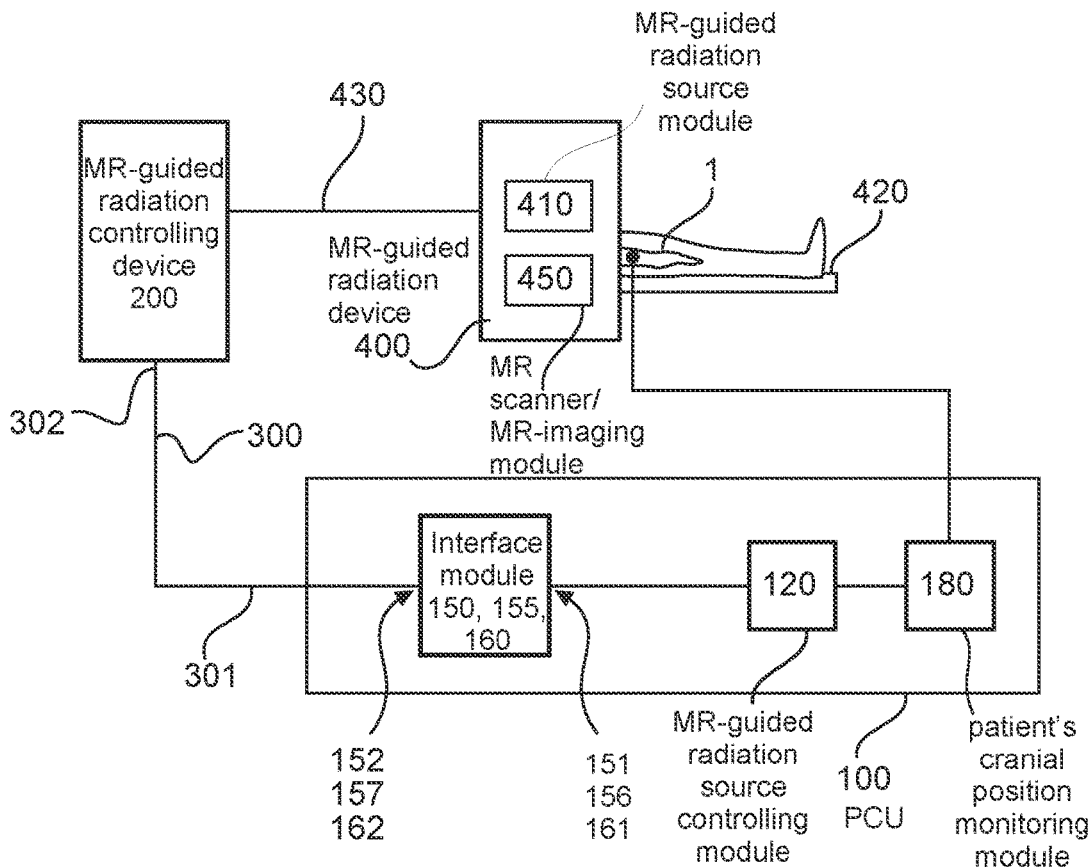
FIG. 1 illustrates an exemplary and schematic buildup of an MR-guided radiation system.

FIG. 1 illustrates a general set-up of an MR-guide radiation system which comprises a patient's cranial position monitoring and controlling device 100, an MR-guided radiation controlling device 200 and an MR-guided radiation device 400. The patient's cranial position monitoring and controlling device 100, also referred to as PCU, is connected to the MR-guided radiation controlling device 200, also referred to as MRgR-C device, via the signal communication line 300. The MR-guided radiation controlling device 200 is connected to the MR-guided radiation device 400 via the signal communication line 430. A patient 1 to be treated or to be investigated may rest on a carrier 420 of the MR-guided radiation device 400. The patient 1, in particular the head of the patient may rest in an area of the MR-guided radiation device 400, which may be radiated by an MR-guided radiation source of an MR-guided radiation source module 410, for example for a tumor treatment. The MR-guided radiation may be carried out by support of an MR-imaging of the respective area by an MR scanner or MR-imaging module 450. The controlling of the MR-guided radiation source module and the MR-imaging module as well as a signaling may be carried out via the communication line 430 to the MR-guided radiation controlling device 200. The patient resting on the carrier 420 may be monitored with respect to the medical parameters, and in particular to the correct positioning while radiation treatment. The position monitoring may be transmitted to the patient's cranial position monitoring and controlling device 100 in order to then control the MR-guided radiation source module 410 via the MR-guided radiation controlling device 200. For this purpose, the patient's cranial position monitoring and controlling device 100 comprises an MR-guided radiation controlling module 120 and a patient's cranial position monitoring module 180 as well as an interface module 150, 155, 160. The interface module 150, 155, 160 is connected with respect to an inward communication to the MR-guided radiation controlling module 120 and with respect to an outward communication to the MR-guided radiation controlling device 200 to be connected via the communication line 300. Further, the patient's cranial position monitoring module 180 is connected to the MR-guided radiation controlling module 120 in order to provide the MR-guided radiation controlling module 120 with respective positioning information gained from a patient's cranial position sensing device 190, which is not illustrated in detail in FIG. 1. Based on this position and information, the MR-guided radiation source controlling module 120 may communicate to the MR-guided radiation source module 410 via the MR-guided radiation controlling device 200 a controlling signal or even a shut-down signal. In case it is detected that the patient's position is no longer appropriate to the radiation treatment, the MR-guided radiation source controlling module 120 may shut down the radiation source, in particular the radiation source of the MR-guided radiation source module 410. The patient's cranial position monitoring and controlling device 100 may be located close to the patient, in order to keep the distance for patient position monitoring short. In order to avoid noise or disturbances resulting from a signal transmission from the patient's cranial position monitoring and controlling device 100 to the MR-guided radiation controlling device 200, in particular from signals travelling along the signal communication line 300. The signals coming from the MR-guided radiation controlling module 120 are converted at the interface module 150, 155, 160 from electrical signals into optical signals, from electrical signals into a wireless signal or from electrical signals into filtered electrical signals, depending on the applied interface type, as will be described in the following. The electrical signals entering the inward communication side 151, 156, 161 of the interface module 150, 155, 160 will be converted and the signals will leave the interface module in the outward direction 152, 157, 162 as an optical signal, as a wireless signal or as a filtered signal to the first end 301 of the signal communication line 300 and then will enter to the second end 302 of the signal communication line to the MR-guided radiation controlling device 200. Thus, the impact from a transferred signal travelling along the signal communication line 300 may be reduced, in particular as the signals on the signal communication line can be in a way that they do not contain the relevant electromagnetic noise which may impact the MR-imaging on the MR scanner or MR-imaging module 450 of the MR-guided radiation device 400.

Figure 2:
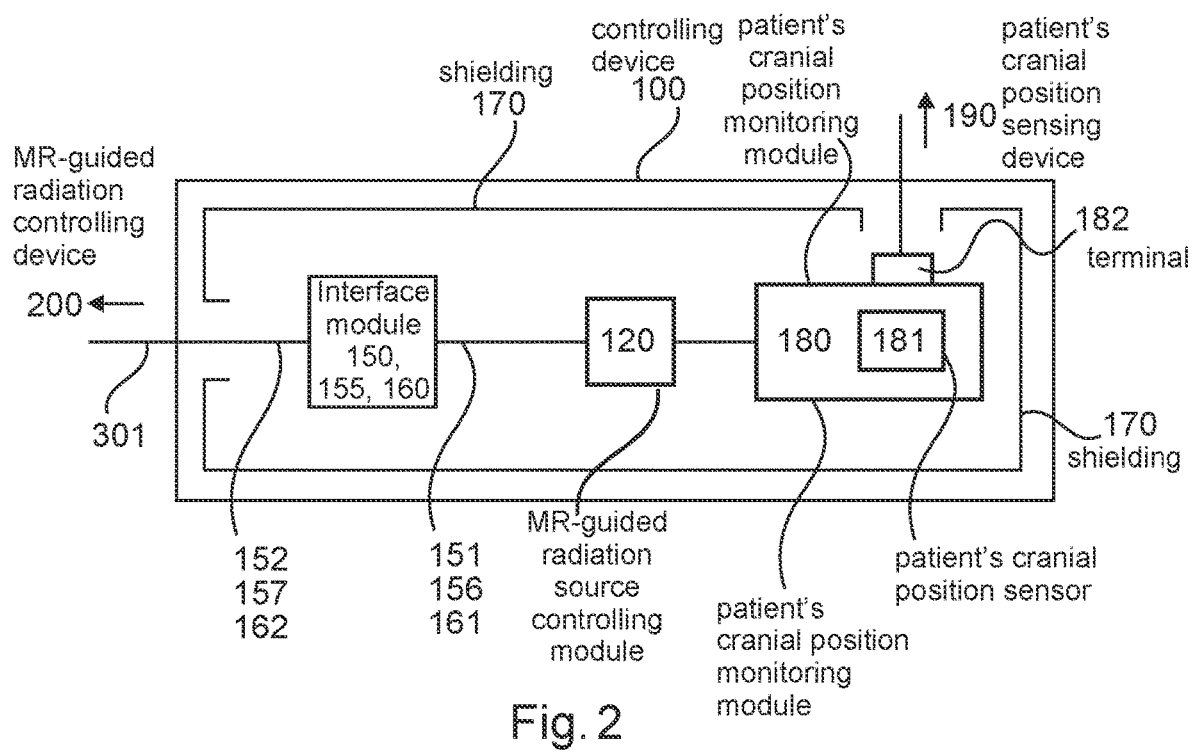
FIG. 2 illustrates an exemplary embodiment of a patient's cranial position monitoring and controlling device.

FIG. 2 illustrates in more details about the patient's cranial position monitoring and controlling device 100. The patient's cranial position monitoring and controlling device 100 includes the above-mentioned MR-guided radiation controlling module 120 and the patient's cranial position monitoring module 180. Both modules are connected to each other so that the patient's cranial position monitoring module 180 may provide the MR-guided radiation controlling module 120 with a respective signaling received from a patient's positioning, in particular form a cranial position sensing device 190, to be connected to the terminal 182 of the patient's cranial position module 180. The signals entering the terminal 182 may be sensed by a patient's cranial position sensor 181 so as to provide a respective signaling to the MR-guided radiation controlling module 120. In case, the patient's cranial position sensing device 190 is an only pressure operated device, a pressure change may be provided to the patient's cranial position monitoring module 180 via the terminal 182, so that a pressure change may be detected by the patient's cranial position sensor 181 which may be a pressure sensor. The MR-guided radiation controlling module 120 may provide the signaling to an MR-guided radiation controlling device 200 to be connected via a signal communication line 300 a first end 301 of which is connected to the outward side 152, 157, 162 of the interface module 150, 155, 160. The patient's cranial position monitoring and controlling device 100 may further be provided with a shielding or shielding cover 170 which may be a shielding of foils with high permeability, a metal shielding, in particular a metal sheet shielding, or any other shielding with respect to the electric or magnetic field being generated within the patient's cranial position monitoring and controlling device. The attenuation of the shielding may be in the field of more than 100 dB, so that any significant impact resulting from the internal components of the patient's cranial position monitoring and controlling device 100 on to an MR-imaging can be avoided.

Figure 3:
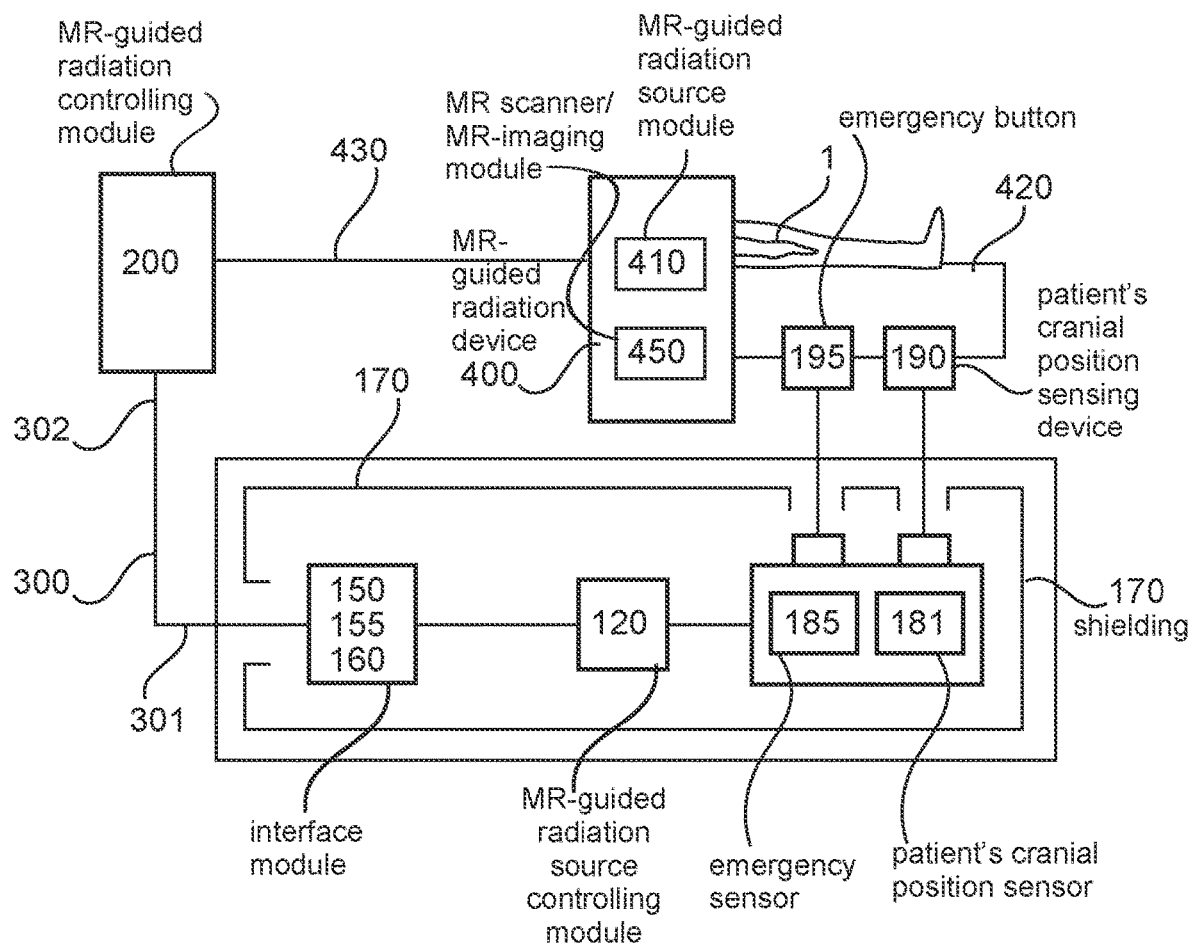
FIG. 3 illustrates a more detailed setup of a patient's cranial position monitoring and controlling device in the environment of an MR-guided radiation system.

FIG. 3 illustrates the patient's cranial position monitoring and controlling device 100 of FIG. 2 in the environment of the entire MR-guided radiation system. As can be seen from FIG. 3, the signals from the MR-guided radiation source controlling module 120, which are converted or filtered in the interface 150, 155, 156, enter the data communication line 300 at the first end 301 and exit the data communication line 300 on the second and 302 at the side of the MR-guided radiation controlling device 200. The MR-guided radiation controlling device 200 controls the MR-guided radiation therapy conducted by the MR-guided radiation device 400 via a signal communication line 430. A patient 1 resting on a carrier 420 of the MR-guided radiation device 400 may be position-monitored by a patient's cranial position sensing device 190 being provided at the patient's side. The signal indicating the patient's position will be transferred to the patient's cranial position monitoring and controlling device 100 and enters the patient's cranial position monitoring module 180 to be sensed by a patient's cranial position sensor 181. In particular, if the signal transmission between the patient's cranial position sensing device 190 and the patient's cranial position monitoring module 180 can be conducted without any electrical line, an impact on the MR-imaging can be avoided. The positioning result will be evaluated, so that based on this evaluation the MR-guide radiation source controlling module 120 may control the MR-guided radiation source module 410 via the MR-guided radiation controlling device 200. This may also include a shutdown of the MR-guided radiation source module 410 in case that it is detected that the position of the patient 1 is no longer appropriate. It should be noted, that the device can be particularly applied to a patient's head treatment by an MR-guided radiation, so that the patient's cranial position sensing device 190 is focused on detecting the patient's cranial position. The shielding cover 170 of the patient's cranial position monitoring and controlling device 100 protects the MR-imaging from being effected by any electric or magnetic field resulting from the internal components of the patient's cranial position monitoring and controlling device 100. As the lines entering the patient's cranial position monitoring and controlling device 100 on both sides, i.e. line 192 on the side of the patient's cranial position monitoring module 180 as well as line 300 on the side of the interface module 150, 155, 160, can be lines without any impact on the MR-imaging, the MR-imaging can be improved and kept free from any noise impact resulting from a patient's cranial position monitoring and controlling device 100, which is arranged close to the MR-imaging module, in particular the MR-scanner/MR-imaging module 450.

It should be noted that the MR-guided radiation source controlling module 120, the patient's cranial position monitoring module 180 and the interface modules 150, 155, 160 are to be understood as functional units, rather than physically separated entities, although it is not excluded to provide those modules as separate physical entities. Further, it should be noted that the signal communication line 300 may be an electrical communication line, an optical communication line or a wireless, i.e. radio communication line. If using the electrical communication line, the used frequency of the signal and/or if using a modulation of the carrier should be in a field which does not generate noise for which the MR-imaging devices are sensitive.

Figure 4:
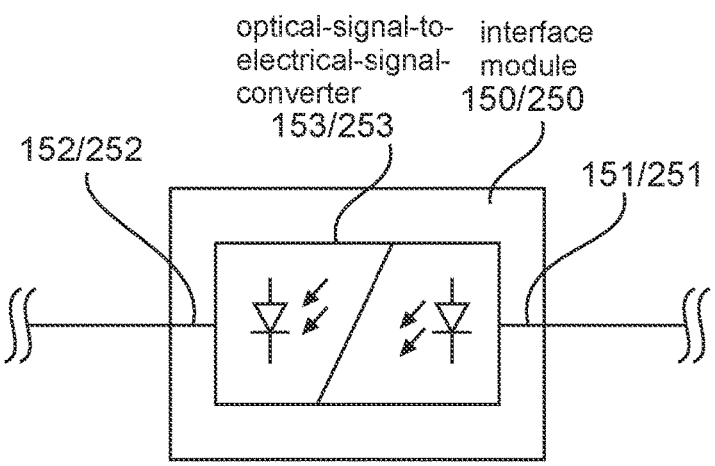
FIG. 4 illustrates an exemplary embodiment of an interface module having an optical/signal converter or converting module.
Figure 5:
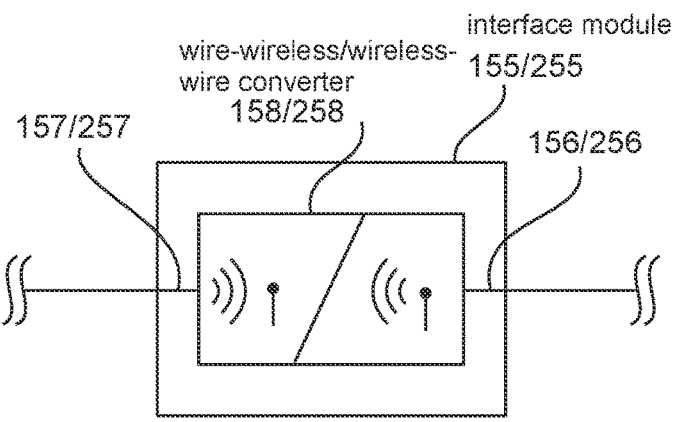
FIG. 5 illustrates an exemplary embodiment of an interface module having a wire/wireless converter or converting module.
Figure 6:
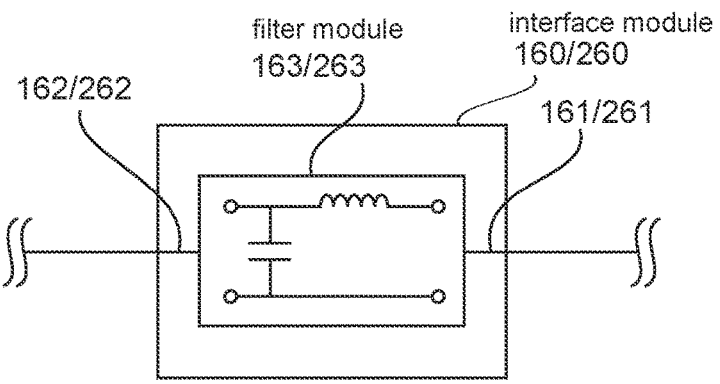
FIG. 6 illustrates an exemplary embodiment of an interface module having a filter module.

It should be noted, that all explanations with respect to FIGS. 4, 5 and 6 referring to the interface modules 150, 155, 160 of the patient's cranial position monitoring and controlling device 100 also apply to the interface modules 250, 255, 260 of the MR-guided radiation controlling device 200. However, in the following, the explanation is carried out referring to the interface modules of the patient's cranial position monitoring and controlling device 100 and it is to be understood that this explanation also applies to the interface modules of the MR-guided radiation controlling device 200.

FIG. 4 illustrates an exemplary embodiment of an interface module 150 of the patient's cranial position monitoring and controlling device 100. In FIG. 4, the interface module 150 includes an optical-signal-to-electrical-signal-converter 153 being capable of converting an electrical signal into an optical signal and vice versa. An electrical signal enters from the inward side of the converter 151, and then is converted into an optical signal and leaves the converter 153 through the outward side 152 of the converter 153. A signal entering from the other side, i.e. an optical signal entering the outward side 152 will then be converted from an optical signal into an electrical signal and will exit the converter 153 through the inward side 151.

FIG. 5 illustrates a corresponding interface module based on a wireless communication. The interface 155 of FIG. 5 comprises a wire-wireless/wireless-wire converter 158 which is capable of converting an electrical signal entering from the inward side 156 into a wireless signal exiting on the outward side 157. It should be noted, that the line illustrated in FIG. 5 does not mean that this is a physical conductive or electric line, but only illustrates the path of the signal which is transmitted wireless.

FIG. 6 illustrates an interface module 160 having a filter module 163. The signal entering the inward side 161 will be filtered and will exit the interface 160 on the outward side 162 as a filtered signal, which filtered signal does not have a significant impact on the MR-imaging of the MR scanner or MR-imaging module 450, which is illustrated in FIGS. 1 and 3. With respect to the filtering, the MR-imaging artifacts free frequency may be in the field of +/−500 kHz bandwidth of corresponding imaging sensing frequency.

In case of a 1.5 T MR scanner or MR-imaging module, the imaging sensing frequency would be about 63.87 MHz+/−500 kHz. In case of a 3.0 T MR scanner or MR-imaging module, the imaging sensing frequency would be 127.74 MHz+/−500 kHz. For the purpose outlined above, it can be used a low-pass filter, a stop-band filter with at least −10 dB at an MR-imaging sensing frequency. The filter may be a higher order Chebyshev or Cauer low-pass filter based on passive components such as inductors and capacitors.

As an alternative, a high order low-pass filter based on resistors and capacitors can be used or a higher order electric low-pass filter based on inductors and capacitors, which generally is known to the skilled person, but may be adapted to the relevant frequencies.

Figure 7:
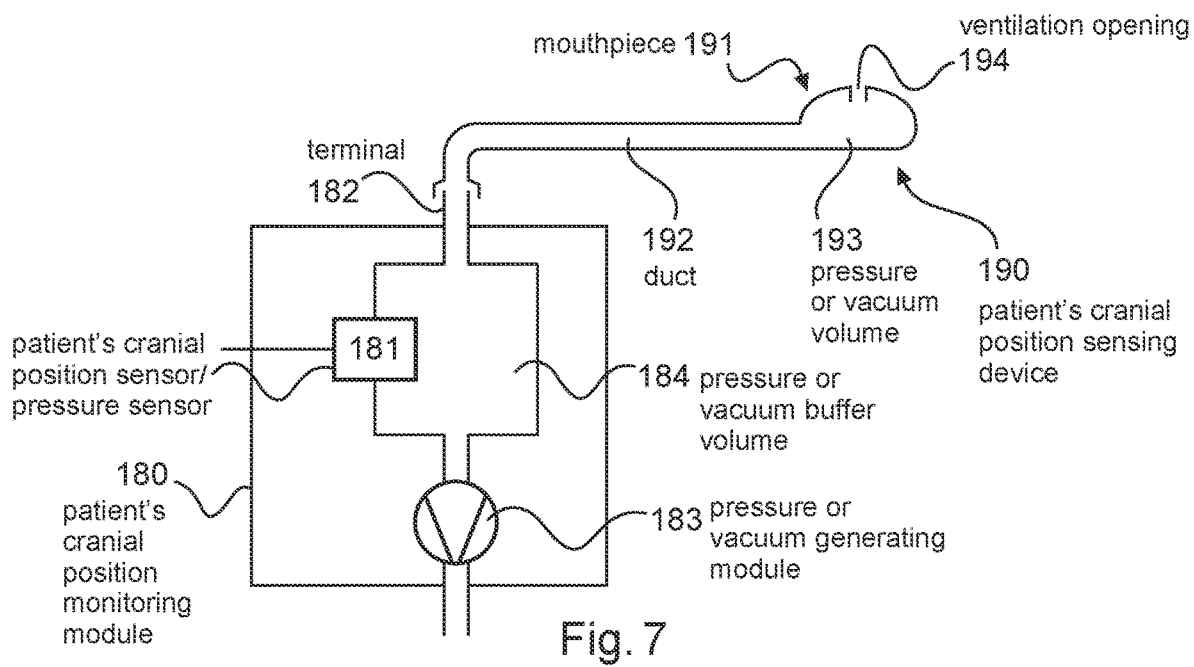
FIG. 7 illustrates an exemplary embodiment of a patient's cranial position monitoring module having coupled thereto a patient's cranial position sensing device.

FIG. 7 illustrates a further detail of the patient's cranial position monitoring module 180 of the patient's cranial position monitoring and controlling device 100. The patient's cranial position monitoring module 180 may include a pressure or vacuum buffer volume 184 which may be evacuated or pressurized by a pressure or vacuum generating module 183. In general, it should be noted, that pressure may mean a positive or a negative pressure which means a vacuum or a positive pressure. The patient's cranial position sensor, in particular a pressure sensor 181 may be connected to the pressure or vacuum buffer volume 184 for detecting the pressure in the pressure or vacuum buffer volume 184. A terminal 182 is provided in order to couple an external patient's cranial position sensing device 190, which will be described below. In case a pressure change is detected in the pressure or vacuum buffer volume 184, the pressure sensor 181 may detect the pressure change and may transfer a respective signal to the MR-guided radiation source controlling module 120 as an indication for a positioning change of a patient. The patient's cranial position sensing device 190 may be connected to the terminal 182. The patient's cranial position sensing device 190 may be a device which does not have any electrical or magnetic components. Further, the patient's cranial position sensing device 190 may have a pressure or vacuum volume 193, which may be provided as a mouth piece to be positioned in a patient's mouth. The pressure or vacuum volume 193 may have a ventilation opening formed therein 194 which may be covered by a patient's mouth or in particular the patient's palate. In case the ventilation opening 194 is covered by a patient's anatomy, the pressure or vacuum volume 193 is closed and the respective pressure level will be the same in the pressure or vacuum buffer volume 184 as both volumes 193 and 184 are in communication via the duct 192. In case the ventilation opening 194 is no longer covered by the patient's anatomy, which is an indication for a release of the patient from the predetermined position, the pressure in the pressure or vacuum volume 193 changes which will also result in a change in the pressure in the pressure or vacuum buffer volume 184, which may be detected by the patient's cranial position sensor 181. Thus, in case the patient's anatomy no longer covers the ventilation opening 194, a respective positioning signal can be detected by the sensor 181 and be provided to the MR-guided radiation source controlling module 120 which then may shut down the radiation source.

Figure 8:
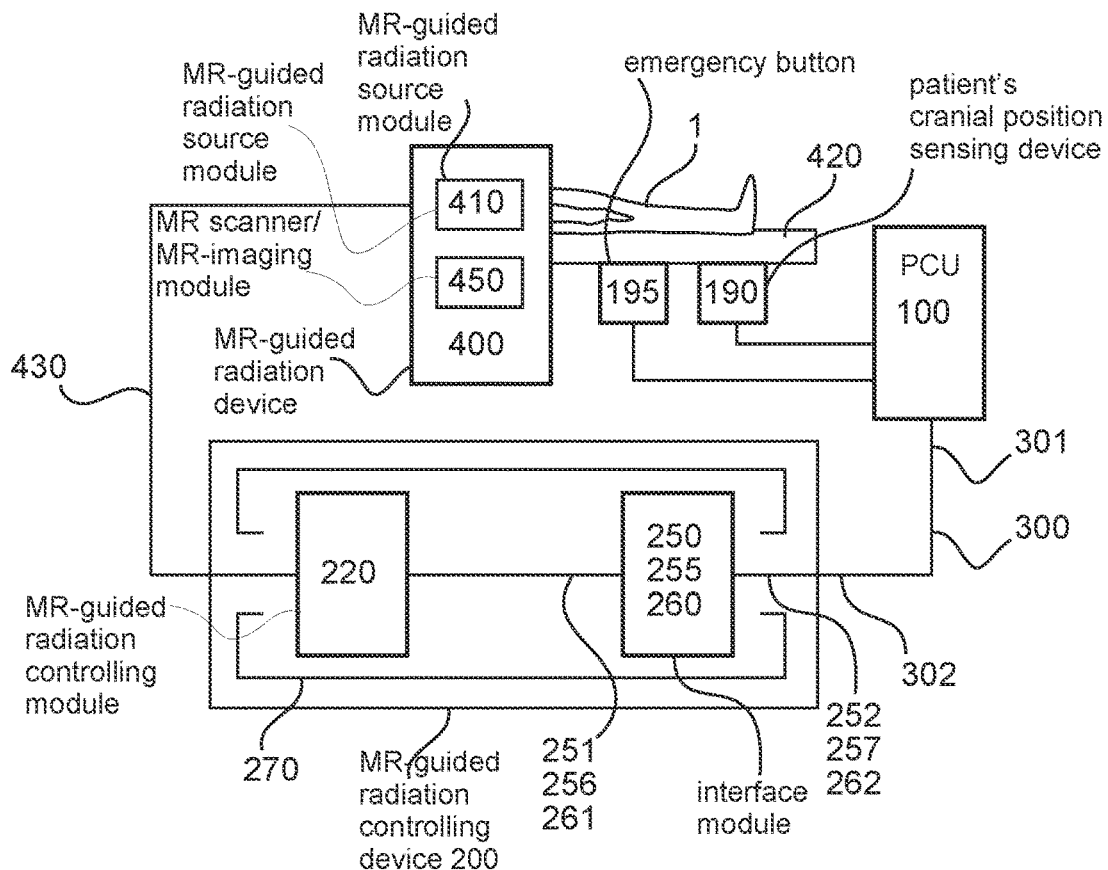
FIG. 8 illustrates and MR-guided radiation controlling device in the environment of an MR-guided radiation system according to an exemplary embodiment.

FIG. 8 illustrates the MR-guided radiation system with a focus on the MR-guided radiation controlling device 200. The MR-guided radiation controlling device 200 may be coupled to the patient's cranial position monitoring and controlling device 100 via the communication line 300 as described above. The MR-guided radiation controlling device 200 may have an interface module 250, 250, 260 which may convert the signal transferred via the communication line 300 back into an electrical signal on the inward side 251, 256, 261. The interface module 250, 255, 260 may be similar or identical interface modules as described with respect to FIGS. 4, 5 and 6. A signal exiting the interface module 250, 255, 260 at the inward side 251, 256, 261 then will enter an MR-guided radiation controlling module 220 which then may control or signal a shutdown of the MR-guided radiation source module 410 via the signal communication line 430. As described above, this shutdown can be carried out based on a patient position monitoring of the patient's cranial position sensing device 190.

Figure 9:
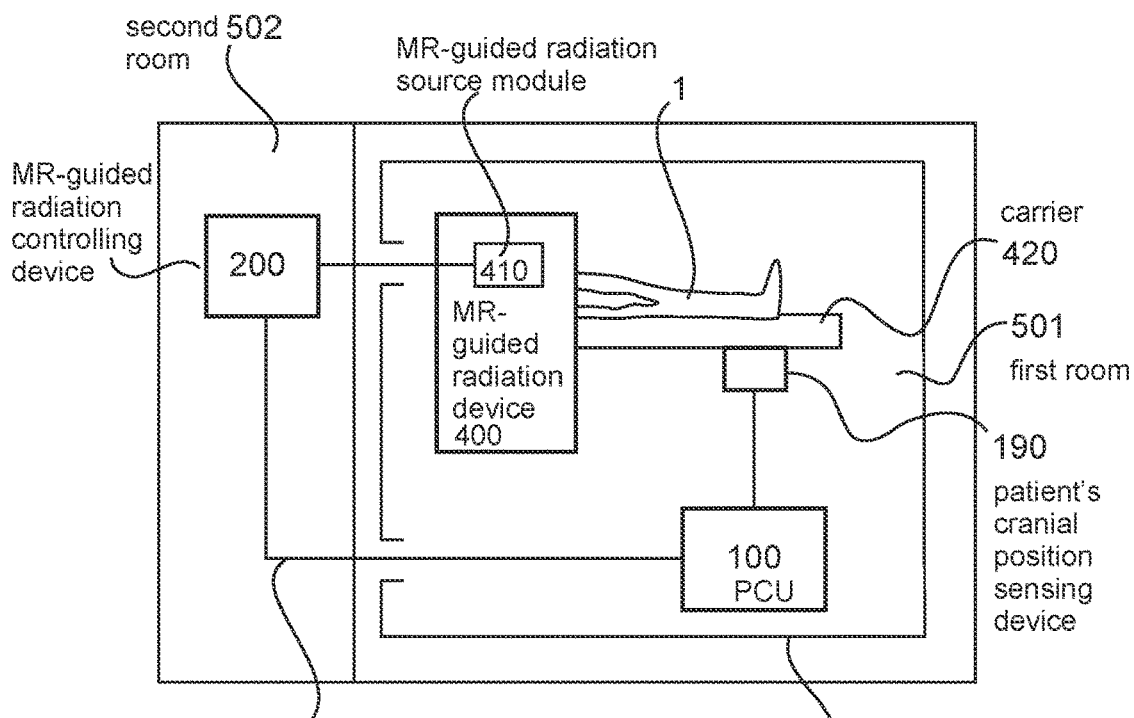
FIG. 9 illustrates a special setup of a first and second room and the components located therein with respect to an exemplary embodiment.

FIG. 9 illustrates a general set-up of the rooms for an MR-guided radiation system. The system may have two rooms, a first room 501 where the patient 1 is located as well as the MR-guided radiation device 400 and the patient's cranial position monitoring and controlling device 100. As the patient's cranial position monitoring and controlling device 100 is designed to not emit any noise which may impact the MR-imaging, the patient's cranial position monitoring and controlling device 100 may be located in the room 501, i.e. close to the patient 1. The MR-guided radiation controlling device 200 may be located in the second room 502 which may be shielded over the first room 501 by a shielding 570. The communication line 300 transits the shielding 570, so that any impact from the MR-guided radiation controlling device 200 onto the MR-imaging can be avoided. It should be noted, that the same principle which applies to the signal communication between the patient's cranial position monitoring and controlling device 100 and the MR-guided radiation controlling device 200 also may apply to a communication between the MR-guided radiation controlling device 200 and the MR-guided radiation device 400 and the components 410 and 450. Consequently, all aspects of signal communication line 300 also may apply for the signal communication line 430. Thus, any impact from electrical components of the patient's cranial position monitoring and controlling device 100 onto an MR-imaging can be avoided.

Figure 10:
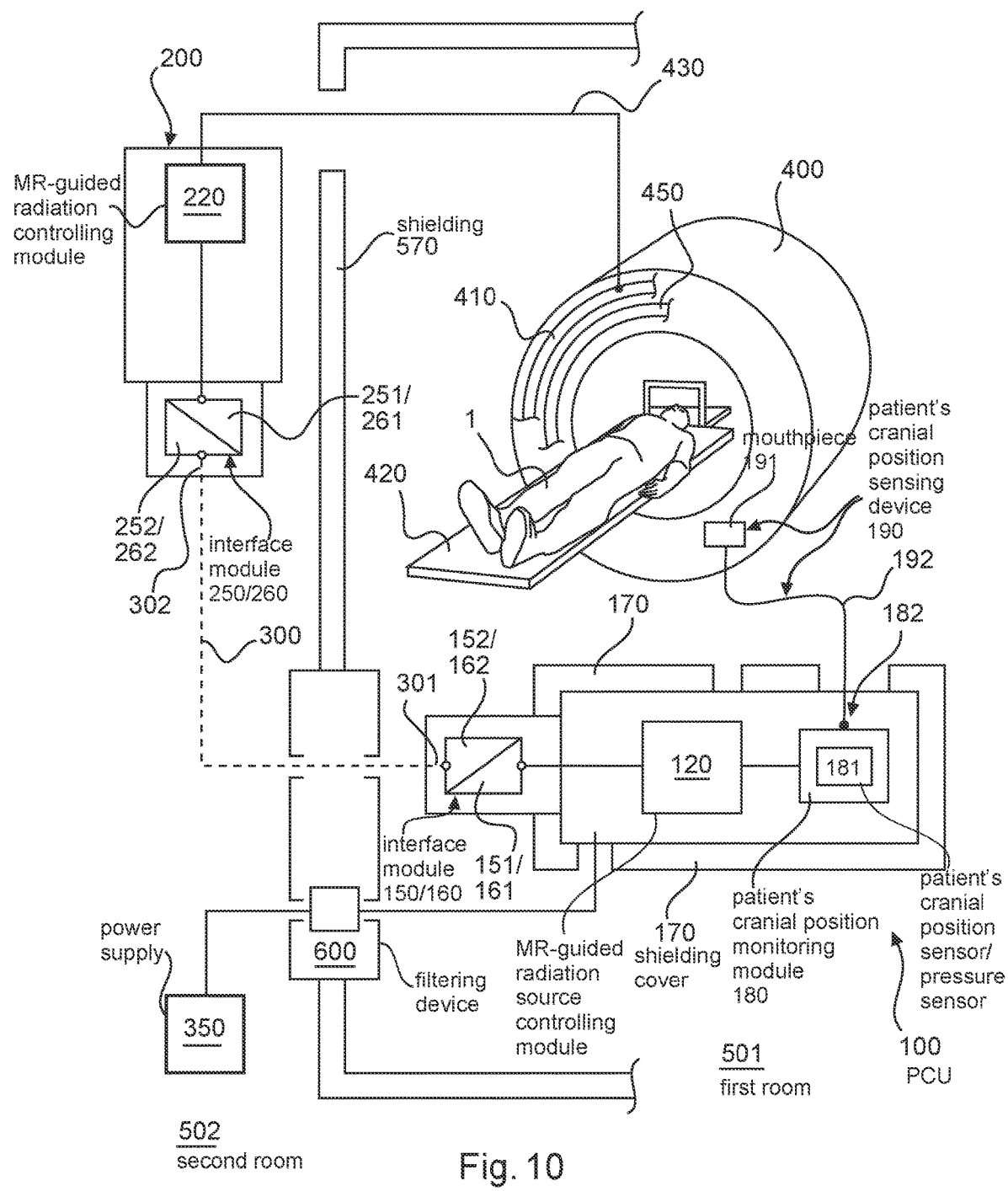
FIG. 10 illustrates an overview of the components of the MR-guided radiation system and components relating to the MR-guided radiation system according to an exemplary embodiment.

FIG. 10 illustrates the entire set-up of the system with all components described above. The patient's cranial position monitoring and controlling device 100 may be provided with power by a power source 350, which may be located in the second room 502. The power communication line may run through a filtering unit 600 in order to filter out MR-imaging relevant noise. The patient's cranial position monitoring and controlling device 100 may also be provided with a battery power supply. In this case, no external power supply is required. The patient's cranial position monitoring and controlling device 100 may also be supplied with both, a battery power supply and a grid power supply. The grid power supply may charge the battery during inactive MR imaging periods and may automatically be switched off upon activation of MR imaging periods, so that the MR imaging relevant noise may be reduced.

REFERENCE LIST

1 patient
100 patient's cranial position monitoring and controlling device (also referred to as PCU)
120 MR-guided radiation source controlling module of PCU
150 interface module of PCU, in particular optical/electrical interface
151 inward side of optical-signal-to-electrical-signal-converter of PCU
152 outward side of optical-signal-to-electrical-signal-converter of PCU
153 optical-signal-to-electrical-signal-converter of PCU
155 interface module of PCU, in particular wireless interface
156 inward side of wire-wireless/wireless-wire converter of PCU
157 outward side of wire-wireless/wireless-wire converter of PCU
158 wire-wireless/wireless-wire converter of PCU
160 interface module of PCU, in particular filter interface
161 inward side of filter module/filter interface of PCU
162 outward side of filter module/filter interface of PCU
163 filter module of PCU
170 shielding cover of PCU
180 patient's cranial position monitoring module of PCU
181 patient's cranial position sensor/pressure sensor of PCU
182 terminal of PCU for a patient's cranial position sensing device
183 pressure or vacuum generating module
184 pressure or vacuum buffer volume
185 emergency sensor of patient's cranial position monitoring module of PCU
186 terminal of PCU for an emergency button
190 patient's cranial position sensing device
191 mouthpiece of patient's cranial position sensing device
192 duct of patient's cranial position sensing device
193 pressure or vacuum volume/of mouth piece
194 ventilation opening of pressure or vacuum volume/mouth piece
195 emergency button
200 MR-guided radiation controlling device (also referred to as MRgR-C device)
220 MR-guided radiation controlling module of MRgR-C device
250 interface module of MRgR-C device, in particular optical/electrical interface
251 inward side of optical-signal-to-electrical-signal-converter of MRgR-C device
252 outward side of optical-signal-to-electrical-signal-converter of MRgR-C device
253 optical-signal-to-electrical-signal-converter of MRgR-C device
255 interface module of MRgR-C device, in particular wireless interface
256 inward side of wire-wireless/wireless-wire converter of MRgR-C device 257 outward side of wire-wireless/wireless-wire converter of MRgR-C device
258 wire-wireless/wireless-wire converter of MRgR-C device
260 interface module of MRgR-C device, in particular filter interface
261 inward side of filter module/filter interface of MRgR-C device
262 outward side of filter module/filter interface of MRgR-C device
263 filter module of MRgR-C device
270 shielding cover of MRgR-C device
300 signal communication line
301 first end of signal communication line
302 second end of signal communication line
350 power supply for PCU
400 MR-guided radiation device
410 MR-guided radiation source module of MR-guided radiation device
420 carrier of MR-guided radiation device
430 signal communication line between MRgR-C device and MR-guided radiation device
450 MR scanner/MR-imaging module of MR-guided radiation device
501 first room of MR-guided radiation system
502 second room of MR-guided radiation system
570 shielding of first room of MR-guided radiation system
600 filtering device for power supply for PCU

The invention claimed is:

1. A cranial position monitoring and controlling device for use during a magnetic resonance (MR) guided radiation treatment process for a patient, the cranial position monitoring and controlling device comprising:
a communications interface that connects the cranial position monitoring and controlling device to a position sensing device and a radiation controlling device;
one or more circuits configured to:
receive an input signal from the position sensing device indicating a cranial position of the patient during the MR-guided radiation treatment process;
generate an output signal for controlling a radiation source used in the MR-guided radiation treatment process for the patient based on the input signal;
filter the output signal using a low-pass filter or a stop-band filter to remove MR-imaging relevant noise produced within the cranial position monitoring and controlling device from the output signal;
provide the output signal to the radiation controlling device such that the radiation controlling device controls the radiation source used in the MR-guided radiation treatment process for the patient based on the output signal; and
a position sensor that receives the input signal from the position sensing device;
wherein the one or more circuits are further configured to provide a positive pressure or a negative pressure to the position sensing device based on the cranial position of the patient;
wherein the position sensing device comprises a pressure volume, a pressure sensor, a duct connecting the pressure volume to the cranial position monitoring and controlling device, and a ventilation opening formed in the pressure volume, wherein the pressure sensor detects a pressure change in the pressure volume depending on a coverage of the ventilation opening; and
wherein the position sensing device is a mouthpiece having the pressure volume formed therein and connected to the cranial position monitoring and controlling device via the duct, wherein the mouthpiece also has the ventilation opening formed therein so that when the mouthpiece is in a predetermined position, the ventilation opening is covered by an anatomy of the patient so that the pressure change occurs in the pressure volume upon release of the anatomy of the patient from the ventilation opening.

2. The device according to claim 1, further comprising an optical-signal-to-electrical-signal-converter circuit configured to convert the output signal from an electrical signal into an optical signal.

3. The device according to claim 1, further comprising a wire-wireless/wireless-wire converter circuit configured to convert the output signal from a wire bound signal to a wireless signal.

4. The device according to claim 1, wherein the one or more circuits are configured to filter the output signal using the stop-band filter with at least a ten decibel reduction of MR-imaging relevant noise.

5. The device according to claim 1, further comprising a shielding cover for attenuating the MR-imaging relevant noise produced within the cranial position monitoring and controlling device for avoiding MR-imaging artiefacts.

6. The device according to claim 1, wherein the one or more circuits are further configured to instruct the radiation controlling device to shut down the radiation source by providing the output signal to the radiation controlling device.

7. The device according to claim 1, wherein the ventilation opening is covered by the anatomy of the patient, and wherein the anatomy of the patient includes a palate of the patient.

8. The device according to claim 1, further comprising an emergency sensor, wherein the one or more circuits are further configured to alter the output signal based on a signal generated by the emergency sensor.

9. The device according to claim 8, wherein the one or more circuits are further configured to instruct the radiation controlling device to shut down the radiation source by providing the output signal to the radiation controlling device.

* * * * *

UNITED STATES PATENT AND TRADEMARK OFFICE
CERTIFICATE OF CORRECTION

PATENT NO. : 11,559,704 B2
APPLICATION NO. : 16/356756
DATED : January 24, 2023
INVENTOR(S) : Rui Liu It is certified that error appears in the above-identified patent and that said Letters Patent is hereby corrected as shown below:

In the Specification

Column 1, Lines 13-14, "resonance image-guided" should be --resonance (MR) image-guided--.

Column 1, Line 31, "MR-imaging" should be --magnetic resonance (MR)-imaging--.

Column 4, Line 36, "in form" should be --in the form--.

Column 8, Line 34, "an MR-guided" should be --a magnetic resonance (MR)-guided--.

In the Claims

Column 16, Claim 5, Line 36, "artiefacts" should be --artifacts--.

Signed and Sealed this
Third Day of September, 2024

Katherine Kelly Vidal
*Director of the United States Patent and Trademark Office*